(12) United States Patent
Malherbe et al.

(10) Patent No.: US 7,728,142 B2
(45) Date of Patent: Jun. 1, 2010

(54) 3-METHANESULFONYLQUINOLINES AS GABA$_B$ ENHANCERS

(75) Inventors: Parichehr Malherbe, Muttenz (CH); Raffaello Masciadri, Basel (CH); Roger David Norcross, Olsberg (CH); Eric Prinssen, Guebwiller (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 1035 days.

(21) Appl. No.: 11/444,770

(22) Filed: Jun. 1, 2006

(65) Prior Publication Data

US 2006/0276469 A1 Dec. 7, 2006

(30) Foreign Application Priority Data

Jun. 2, 2005 (EP) ................... 05104786

(51) Int. Cl.
*C07D 215/38* (2006.01)
(52) U.S. Cl. ............... 546/153; 546/155; 546/156
(58) Field of Classification Search ............. 546/153, 546/155, 156; 514/312
See application file for complete search history.

(56) References Cited

U.S. PATENT DOCUMENTS

| | | | |
|---|---|---|---|
| 4,952,573 A | 8/1990 | LeClerc et al. | |
| 6,313,146 B1 | 11/2001 | Van Wagenen et al. | |
| 6,649,626 B1 | 11/2003 | Dodd et al. | |
| 7,250,515 B2 * | 7/2007 | Chen et al. | 546/135 |

FOREIGN PATENT DOCUMENTS

| | | |
|---|---|---|
| EP | 0 334 491 | 9/1989 |
| EP | 0 345 068 B1 | 12/1989 |
| EP | 0 419 247 | 3/1991 |
| WO | WO 96/14319 | 5/1996 |
| WO | WO 01/29030 | 4/2001 |
| WO | WO 01/56990 | 8/2001 |
| WO | WO 03/080580 | 10/2003 |
| WO | WO 03/090731 | 11/2003 |
| WO | WO 2004/043930 | 5/2004 |
| WO | WO 2005/026125 | 3/2005 |
| WO | WO 2005/040124 | 5/2005 |

OTHER PUBLICATIONS

Hill et al., Nature, 290, pp. 149-152, (1981).
Billinton et al. Trends in Neurosci., 24, 277-282, (2001).
Bowery et al., Pharmacol. Rev.. 54, pp. 247-264, (2002).
Vacher et al., Curr. Drug Targets, CNS Neurol. Disord. 2, pp. 248-259, (2003).
Bettler et al., Physiol Rev. 84, pp. 835-867, (2004).
Kaupmann et al., Nature, 386, pp. 239-246, (1997).
Kaupmann et al., Nature, 396, pp. 683-687, (1998).
Pin et al., Pharmaco.. Ther. 98, pp. 325-354, (2003).
Galvez et al., J. Biol. Chem., 275, pp. 41166-41174, (2000).
Havlickova et al., Mol. Pharmacol. 62, pp. 343-350, (2002).
Kniazeff et al.,J. Neurosci., 22, pp. 7352-7361, (2002).
Schuler et al., Neuron, 31, pp. 47-58, (2001).
Peters et al., Neurogenetics, 2, pp. 47-54, (1998).
Mondabon et al., Am. J. Med. Genet 122B/1, p. 134, (2003).
Gassmann et al., J Neurosci. 24, pp. 6086-6097, (2004).
Misgeld et al., Prog. Neurobiol. 46, pp. 423-462, (1995).
Enna et al., Life Sci, 62, pp. 1525-1530, (1998).
McCarson et al., Neuropharmacology, 38, pp. 1767-1773, (1999).
Brebner et al., Neuropharmacology, 38, pp. 1797-1804, (1999).
Paterson et al., Psychopharmacology, 172, pp. 179-186, (2004).
Breslow et al., Am. J. Psychiatry, 146, pp. 353-356, (1989).
Drake et al., Ann. Pharmacother. 37., pp. 1177-1181, (2003).
Bortolato et al., Psychopharmacology, 171, pp. 322-330, (2004).
Urwyler et al., Mol. Pharmacol., 60, pp. 963-971, (2001).
Pin et al., Mol. Pharmacol.,60, pp. 881-884, (2001).
Binet et al., J Biol Chem., 279, pp. 29085-29091, (2004).
Wigger et al., Neuropsychopharmacology, pp. 1-14, (2004).
Urwyler et al., J. Pharmacol. Exp. Ther., 307, pp. 322-330, (2003).
Cryan et al., J Pharmacol Exp Ther., 310, pp. 952-963, (2004).
Smith et al., Psychopharmacology, 173, pp. 105-111, (2004).
Knoflach et al., Proc. Natl. Acad. Sci., USA, 98, pp. 13402-13407, (2001).
Wichmann et al., Il Farmaco, 57, pp. 989-992, (2002).
Hammerland et al., Mol. Pharmacol., 53, pp. 1083-1088, (1998).
O'Brien et al., J. Pharmaco. Exp. Ther., 309, pp. 568-577 (2004).
Schaffhauser et al., Mol. Pharmacol., 64, pp. 798-810, (2003).
Mombereau et al., Neuropsychopharmacology, 29, pp. 1050-1062, 2004.
Fuson, R.C., et al., J. Am. Chem. Soc., vol. 79, pp. 3477-3480 (1957).
Walser, A., et al., J. Heterocycl. Chem., vol. 13, pp. 131-133 (1976).
Sinsky, M.D., et al., J. Heterocycl. Chem., vol. 21, pp. 759-768 (1984).
Arcadi, A., et al., Synlett., pp. 203-206 (2003).
Sato, Susumu, et al., Chemical Abstract of JP 2002 371078 A2 XP002367441.
Chemical Abstracts, XP002367442, Publ. Date Apr. 25, 2003.
Chemical Abstracts, XP002367443, Publ. Date Sep. 27, 2004.
Urwyler, S., et al., Molecular Pharmacology, vol. 60, No. 5, Nov. 2001, pp. 963-971.

(Continued)

Primary Examiner—D. Margaret Seaman
(74) Attorney, Agent, or Firm—George W. Johnston; Patricia S. Rocha-Tramaloni; Kimberly J. Prior

(57) ABSTRACT

The present invention relates to compounds of formula I

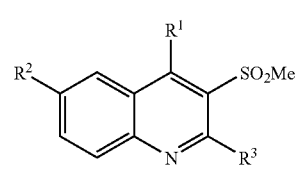

wherein $R^1$, $R^2$ and $R^3$ are as defined in the specification, which are active at the GABA$_B$ receptor and which can be used for the treatment of CNS disorders.

24 Claims, No Drawings

OTHER PUBLICATIONS

Urwyler, S., et al., American Chemical Society, Abstracts of Paper at the National Meeting of the ACS, Washington, D.C., vol. 225, No. 1/2, Mar. 23, 2003, p. MEDI 317.

Mohamed, et al., *Synthesis and antimicrobial activity of some newer 6-iodo-2-methyl-3-substituted 4(3H)-quinazolinones*, J. Serb. Chem. vol. 57(10) pp. 629-633 (1992) XP002397916.

* cited by examiner

3-METHANESULFONYLQUINOLINES AS GABA$_B$ ENHANCERS

PRIORITY TO RELATED APPLICATIONS

This application claims the benefit of European Application No. 05104786.8, filed Jun. 2, 2005, which is hereby incorporated by reference in its entirety.

BACKGROUND OF THE INVENTION

γ-Aminobutyric acid (GABA), the most abundant inhibitory neurotransmitter, activates both ionotropic GABA$_{A/C}$ and metabotropic GABA$_B$ receptors (Hill and Bowery, Nature, 290, 149-152, 1981). GABA$_B$ receptors that are present in most regions of the mammalian brain on presynaptic terminals and postsynaptic neurons are involved in the fine-tuning of inhibitory synaptic transmission. Presynaptic GABA$_B$ receptors through modulation of high-voltage activated Ca$^{2+}$ channels (P/Q- and N-type) inhibit the release of many neurotransmitters. Postsynaptic GABA$_B$ receptors activates G-protein coupled inwardly rectifying K+ (GIRK) channel and regulates adenylyl cyclase (Billinton et al., Trends Neurosci., 24, 277-282, 2001; Bowery et al., Pharmacol. Rev. 54, 247-264, 2002). Because the GABA$_B$ receptors are strategically located to modulate the activity of various neurotransmitter systems, GABA$_B$ receptor ligands hence could have potential therapeutic applications in the treatment of anxiety, depression, epilepsy, schizophrenia and cognitive disorders (Vacher and Bettler, Curr. Drug Target, CNS Neurol. Disord. 2, 248-259, 2003; Bettler et al., Physiol Rev. 84, 835-867, 2004).

Native GABA$_B$ receptors are heteromeric structures composed of two types of subunits, GABA$_B$R1 and GABA$_B$R2 subunits (Kaupmann et al., Nature, 386, 239-246, 1997 and Nature, 396, 683-687, 1998). The structure of GABA$_B$R1 and R2 show that they belong to a family of G-protein coupled receptors (GPCRs) called family 3. Other members of the family 3 GPCRs include the metabotropic glutamate (mGlu1-8), Calcium-sensing, vomeronasal, pheromone and putative taste receptors (Pin et al., Pharmaco. Ther. 98, 325-354, 2003). The family 3 receptors (including GABA$_B$ receptors) are characterized by two distinctly separated topological domains: an exceptionally long extracellular amino-terminal domain (ATD, 500-600 amino acids), which contains a venus flytrap module for the agonist binding (orthosteric site) (Galvez et al., J. Biol. Chem., 275, 41166-41174, 2000) and the 7TM helical segments plus intracellular carboxyl-terminal domain that is involved in receptor activation and G-protein coupling. The mechanism of receptor activation by agonist in GABA$_B$R1R2 heterodimer is unique among the GPCRs. In the heteromer, only GABA$_B$R1 subunit binds to GABA, while the GABA$_B$R2 is responsible for coupling and activation of G-protein (Havlickova et al., Mol. Pharmacol. 62, 343-350, 2002; Kniazeff et al., J. Neurosci., 22, 7352-7361, 2002).

Schuler et al., Neuron, 31, 47-58, 2001 have demonstrated that the GABA$_B$R1 knock-out (KO) mice exhibit spontaneous seizures and hyperalgesia. These KO mice have lost all the biochemical and electrophysiological GABA$_B$ responses. Interestingly, the GABA$_B$R1 KO mice were more anxious in two anxiety paradigm, namely the light-dark box (decreased time in light) and staircase tests (decreased rears and steps climbed). They showed a clear impairment of passive avoidance performance model indicating impaired memory processes. The GABA$_B$R1 KO also displayed increased hyperlocomotion and hyperactivity in new environment. The GABA$_B$R1 gene is mapped to chromosome 6p21.3, which is within the HLA class I, a region with linkage for schizophrenia, epilepsy and dyslexia (Peters et al., Neurogenetics, 2, 47-54, 1998). Mondabon et al., Am. J. Med. Genet 122B/1, 134, 2003 have reported about a weak association of the Ala20Val polymorphism of GABA$_B$R1 gene with schizophrenia. Moreover, Gassmann et al., J Neurosci. 24, 6086-6097, 2004 has shown that GABA$_B$R2KO mice suffer from spontaneous seizures, hyperalgesia, hyperlocomotor activity and severe memory impairment, comparable to GABA$_B$R1KO mice. Therefore, heteromeric GABA$_B$R1R2 receptors are responsible for these phenotypes.

Baclofen (Lioresalθ, β-chlorophenyl GABA), a selective GABA$_B$ receptor agonist with EC$_{50}$=210 nM at native receptor, is the only ligand, which has been used since 1972 in clinical study for the treatment of spasticity and skeletal muscle rigidity in patients following spinal cord injury, multiple sclerosis, amyotrophic lateral sclerosis, cerebral palsy. Most of the preclinical and clinical studies conducted with baclofen and GABA$_B$ receptor agonists were for the treatment of neuropathic pain and craving associated with cocaine and nicotine (Misgeld et al., Prog. Neurobiol. 46, 423-462, 1995; Enna et al., Life Sci, 62, 1525-1530, 1998; McCarson and Enna, Neuropharmacology, 38, 1767-1773, 1999; Brebner et al., Neuropharmacology, 38, 1797-1804, 1999; Paterson et al., Psychopharmacology, 172, 179-186, 2003). In panic disorder patients, Baclofen was shown to be significantly effective in reducing the number of panic attacks and symptoms of anxiety as assessed with the Hamilton anxiety scale, Zung anxiety scale and Katz-R nervousness subscale (Breslow et al., Am. J. Psychiatry, 146, 353-356, 1989). In a study with a small group of veterans with chronic, combat-related post-traumatic stress disorder (PTSD), baclofen was found to be an effective and well-tolerated treatment. It resulted in significant improvements in the overall symptoms of PTSD, most notably the avoidance, emotional numbing and hyperarousal symptoms and also in reduced accompanying anxiety and depression (Drake et al., Ann. Pharmacother. 37, 1177-1181, 2003). In preclinical study, baclofen was able to reverse the reduction in prepulse inhibition (PPI) of the acoustic startle response induced by dizocilpine, but not by apomorphine in rat PPI model of psychosis (Bortolato et al., Psychopharmacology, 171, 322-330, 2004). Therefore, GABA$_B$ receptor agonist has a potential in the pharmacological therapy of psychotic disorders. Unfortunately, Baclofen has a number of side-effects including the poor blood-brain-barrier penetration, very short duration of action and narrow therapeutic window (muscle relaxation, sedation and tolerance) that limit its utility.

Urwyler et al., Mol. Pharmacol., 60, 963-971, 2001 have reported on a novel class of GABA$_B$ receptor ligands, called positive allosteric modulators, CGP7930 [2,6-di-tert-butyl-4-(3-hydroxy-2,2-dimethyl-propyl)-phenol] and its aldehyde analogue CGP13501. These ligands have no effect on their own at GABA$_B$ receptors, but in concert with endogenous GABA, they increase both the potency and maximal efficacy of GABA at the GABA$_B$R1R2 (Pin et al., Mol. Pharmacol., 60, 881-884, 2001). Interestingly, recent study with CGP7930 (Binet et al., J Biol Chem., 279, 29085-29091, 2004) has shown that this positive modulator activates directly the seven transmembrane domains (7TMD) of GABA$_B$R2 subunit. Mombereau et al., Neuropsychopharmacology, 1-13, 2004 have recently reported on the anxiolytic effects of acute and chronic treatment with the GABA$_B$ receptor positive modulator, GS39783 (N,N_-dicyclopentyl-2-methylsulfanyl-5-nitro-pyrimidine-4,6-diamine) (Urwyler et al., J. Pharmacol. Exp. Ther., 307, 322-330, 2003) in the light-dark box and elevated zero maze test models of anxiety. No tolerance after chronic treatment (21 days) with GS39783 (10 mg/kg, P.O., once daily) was observed. Because the GABA$_B$ enhancers have no effect on receptor activity in the absence of GABA, but do enhance allosterically the affinity of the GABA$_B$ receptor for the endogenous GABA, it is expected that these ligands should have an improved side effect profile as compared to baclofen. Indeed, GS39783 at 0.1-200 mg/kg, PO had no effect on spontaneous locomotor activity, rotarod, body temperature and traction test in comparison to baclofen, which showed these side effects at 2.5-15 mg/kg, PO. GS39783 did not have any effect on cognition performance as assessed by passive avoidance behavioral test in mice and rats. Furthermore, GS39783 exhibited anxiolytic-like effects in the elevated plus maze (rat), elevated zero maze (mice and rats), and the stress-induced hyperthermia (mice) test paradigms. Therefore, GS39783 represents a novel anxiolytic without side-effects associated with baclofen or benzodiazepines (Cryan et al., *J Pharmacol Exp Ther.*, 310, 952-963, 2004). The preclinical investigation with the CGP7930 and GS39783 has shown that both compounds were effective at decreasing cocaine self-administration in rats (Smith et al., *Psychopharmacology*, 173, 105-111, 2004). The positive modulator, CGP7930 has also been preclinically studied for the treatment of Gastro-Esophageal Reflux Disease (GERD) and was found to be effective (WO 03/090731, Use of $GABA_B$ receptor positive modulators in gastro-intestinal disorders).

Positive allosteric modulators have been reported for other family 3 GPCRs including mGlu1 receptor (Knoflach et al., *Proc. Natl. Acad. Sci., USA*, 98, 13402-13407, 2001; Wichmann et al., *Farmaco*, 57, 989-992, 2002), Calcium-sensing receptor (NPS R-467 and NPS R-568) (Hammerland et al., *Mol. Pharmacol.*, 53, 1083-1088, 1998) (U.S. Pat. No. 6,313, 146), mGlu2 receptor [LY487379, N-(4-(2-methoxyphenoxy)-phenyl-N-(2,2,2-trifluoroethylsulfonyl)-pyrid-3-ylm-ethylamine and its analogs] (WO 01/56990, Potentiators of glutamate receptors) and mGlu5 receptor (CPPHA, N-{4-chloro-2-[(1,3-dioxo-1,3-dihydro-2H-isoindol-2-yl)methyl] phenyl}-2-hydroxybenzamide) (O'Brien et al., *J. Pharmaco. Exp. Ther.*, 27, Jan. 27, 2004). Interestingly, it has been demonstrated that these positive modulators bind to a novel allosteric site located within the 7TMD region, thereby enhancing the agonist affinity by stabilizing the active state of the 7TMD region (Knoflach et al., *Proc. Natl. Acad. Sci., USA* 98, 13402-13407, 2001; Schaffhauser et al., *Mol. Pharmacol.*, 64, 798-810, 2003). Moreover, the NPS R-467, NPS R-568 (Tecalcet) and related compounds represent the first positive allosteric modulators that entered the clinical trails due to their allosteric mode of action.

WO 2003080580, WO 2005026125 and WO 2005040124 describe quinoline derivatives for the treatment of CNS disorders. Nevertheless, the compounds disclosed in these patent applications are 3-aryl/heteroarylsulfonyl-8-piperazine-quinoline derivatives, which derivatives differ from the compounds of the instant invention.

SUMMARY OF THE INVENTION

The present invention provides compounds of formula I

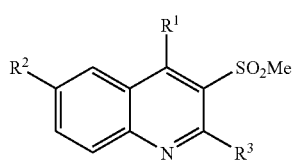

(I)

wherein
$R^1$ is phenyl optionally substituted by one or more substituents selected from the group consisting of Cl, F, $C_{1-7}$-haloalkyl, hydroxy, $C_{1-7}$-alkoxy, $C_{1-7}$-haloalkoxy, di($C_{1-7}$)alkylamino and $C_{1-7}$-alkylsulfonyl, or is 5 or 6 membered heterocycloalkyl optionally substituted by OH;
$R^2$ is Br, I, $C_{1-7}$-alkyl, $C_{1-7}$-alkoxy, $C_{1-7}$-haloalkyl, $C_{1-7}$-haloalkoxy, aryloxy, arylsulfonyl, $C_{3-6}$-cycloalkyl optionally substituted by phenyl, —$NR^aR^b$ wherein $R^a$ and $R^b$ are each independently $C_{1-7}$-alkyl, or $R^a$ and $R^b$, together with the nitrogen atom to which they are attached, form a 4 to 8 membered heterocycloalkyl group which is optionally substituted by one or more substituent(s) selected from the group consisting of halo, $C_{1-7}$-alkyl, $C_{1-7}$-alkoxy, hydroxy, phenyl and di($C_{1-7}$)alkylamino; and
$R^3$ is H, $C_{1-7}$-alkyl, or $C_{3-6}$-cycloalkyl;

and optical isomers and pharmaceutically acceptable salts thereof.

The present invention also provides pharmaceutical compositions containing one or more compound of formula I or a pharmaceutically acceptable salt thereof and a pharmaceutically acceptable carrier. The invention further provides processes for the preparation of the compounds and compositions of the invention. The invention also provides novel intermediates for preparation of compounds of the invention.

The compounds of formula I and their salts are active on the $GABA_B$ receptor and, thus, are distinguished by valuable therapeutic properties. Therefore, the invention provides method for the treatment of CNS disorders, such as anxiety, depression, epilepsy, schizophrenia, cognitive disorders, spasticity and skeletal muscle rigidity, spinal cord injury, multiple sclerosis, amyotrophic lateral sclerosis (ALS), cerebral palsy, neuropathic pain and craving associated with cocaine and nicotine, psychosis, panic disorder, post traumatic stress disorders, and gastro-intestinal disorders.

DETAILED DESCRIPTION OF THE INVENTION

The following definitions of the general terms used in the present description apply irrespective of whether the terms in question appear alone or in combination. It must be noted that, as used in the specification and appended claims, the singular forms "a," "an," and "the" include plural forms unless the context clearly dictates otherwise.

As used herein, the term "aryl" means a monovalent cyclic aromatic hydrocarbon moiety selected from optionally substituted phenyl or naphthyl. Substituents for aryl include but are not limited to halo, hydroxy, $C_{1-7}$-alkyl, $C_{1-7}$-alkoxy, $C_{1-7}$-haloalkyl, $C_{1-7}$-haloalkoxy as well as those groups specifically illustrated in the examples herein below.

The term "aryloxy" denotes an aryl group as defined above which is connected via an oxygen atom. Preferred aryloxy is phenyloxy.

"Arylsulfonyl" denotes an aryl group as defined above which is connected via a sulfonyl group. Preferred arylsulfonyl is phenylsulfonyl.

"$C_{1-7}$-alkyl" denotes a straight- or branched-chain hydrocarbon group containing from 1 to 7 carbon atoms, preferably 1 to 4 carbon atoms. Examples of such groups are methyl, ethyl, propyl, isopropyl, isobutyl, sec-butyl, tert-butyl, pentyl, n-hexyl as well as those specifically illustrated by the examples herein below.

"$C_{1-7}$-haloalkyl" denotes a $C_{1-7}$-alkyl group as defined above which is substituted by one or more halogen atom. Examples of $C_{1-7}$-haloalkyl include, but are not limited to, methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Preferred $C_{1-7}$-haloalkyl are difluoro- or trifluoro-methyl or ethyl.

"$C_{1-7}$-alkoxy" denotes a $C_{1-7}$-alkyl group as defined above which is connected via an oxygen atom. Preferred alkoxy groups are MeO— and Et—O as well as those groups specifically illustrated by the examples herein below.

"$C_{1-7}$-haloalkoxy" denotes a $C_{1-7}$-alkoxy group as defined above which is substituted by one or more halogen atom. Examples of $C_{1-7}$ haloalkoxy include, but are not limited to, methoxy, ethoxy, propoxy, isopropoxy, or isobutoxy substituted by one or more Cl, F, Br or I atom(s) as well as those groups specifically illustrated by the examples herein below. Preferred $C_{1-7}$-haloalkoxy are difluoro- or trifluoro-methoxy or ethoxy groups.

"Halo" or "halogen" denotes chlorine, iodine, fluorine and/or bromine.

"$C_{1-7}$-alkylsulfonyl" denotes a $C_{1-7}$-alkyl group as defined herein above which is connected via a sulfonyl group. Examples of $C_{1-7}$-alkylsulfonyl include, but are not limited to, methylsulfonyl and ethylsulfonyl as well as those groups specifically illustrated by the examples herein below.

The term "di($C_{1-7}$)alkylamino" denotes an —NR$^c$R$^d$ group, wherein R$^c$ and R$^d$ are independently $C_{1-7}$-alkyl groups as defined herein above. Examples of di($C_{1-7}$)alkylamino groups include but are not limited to di(methyl)amino, di(ethyl)amino, methylethylamino, as well as those groups specifically illustrated by the examples herein below.

"Hydroxy" denotes one, two or three —OH group(s).

"$C_{3-6}$-cycloalkyl" denotes a saturated cyclic hydrocarbon ring having 3 to 6 carbon atoms as ring members and includes, but is not limited to, cyclopropyl, cyclobutyl, cyclopentyl, cyclohexyl, as well as those groups specifically illustrated by the examples herein below.

"5 or 6 membered heterocycloalkyl" and "4 to 8 membered heterocycloalkyl" denote a saturated mono- or bi-cyclic ring comprising respectively 5 or 6 or 4 to 8 ring atoms and furthermore containing one, two, or three ring heteroatoms selected from N, O, or S, the remaining ring atoms being C. Preferred 4 to 8 membered heterocycloalkyl groups are 5 or 6 membered heterocycloalkyl groups. Examples include, but are not limited to, optionally substituted azetidinyl, piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiomorpholinyl, thiomorpholinylsulfoxide, thiomorpholinylsulfone, dihydroquinolinyl, dihydrisoquinolinyl, tetrahydroquinolinyl, tetrahydroisoquinolinyl, 1-oxo-thiomorpholin, 1,1-dioxo-thiomorpholin, 1,4-diazepane, 1,4-oxazepane and 8-oxa-3-aza-bicyclo[3.2.1]oct-3-yl, as well as those groups specifically illustrated by the examples herein below. Preferred 5 or 6 membered heterocycloalkyl groups are morpholine or piperidine, in particular morpholin-4-yl or piperidin-1-yl. Substituents for these heterocycloalkyl groups include, but are not limited to, halo, hydroxy, $C_{1-7}$-alkyl, $C_{1-7}$-alkoxy, $C_{1-7}$-haloalkyl, $C_{1-7}$-haloalkoxy as well as those groups specifically illustrated by the examples herein below.

"Pharmaceutically acceptable," such as pharmaceutically acceptable carrier, excipient, etc. means pharmacologically acceptable and substantially non-toxic to the subject which the particular compound is administered.

The term "pharmaceutically acceptable acid addition salts" embraces salts with inorganic and organic acids, which include but are not limited to hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid.

"Therapeutically effective amount" means an amount that is effective to prevent, alleviate, or ameliorate symptoms of disease or prolong the survival of the subject being treated.

The present invention provides compounds of formula I

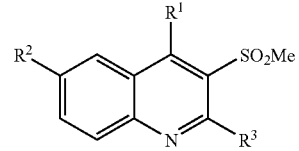

(I)

wherein

R$^1$ is phenyl optionally substituted by one or more substituents selected from the group consisting of Cl, F, $C_{1-7}$-haloalkyl, hydroxy, $C_{1-7}$-alkoxy, $C_{1-7}$-haloalkoxy, di($C_{1-7}$)alkylamino and $C_{1-7}$-alkylsulfonyl, or is 5 or 6 membered heterocycloalkyl optionally substituted by OH;

R$^2$ is Br, I, $C_{1-7}$-alkyl, $C_{1-7}$-alkoxy, $C_{1-7}$-haloalkyl, $C_{1-7}$-haloalkoxy, aryloxy, arylsulfonyl, $C_{3-6}$-cycloalkyl optionally substituted by phenyl, —NR$^a$R$^b$ wherein R$^a$ and R$^b$ are each independently $C_{1-7}$-alkyl, or R$^a$ and R$^b$, together with the nitrogen atom to which they are attached, form a 4 to 8 membered heterocycloalkyl group which is optionally substituted by one or more substituent(s) selected from the group consisting of halo, $C_{1-7}$-alkyl, $C_{1-7}$-alkoxy, hydroxy, phenyl and di($C_{1-7}$)alkylamino; and R$^3$ is H, $C_{1-7}$-alkyl, or $C_{3-6}$-cycloalkyl;

and optical isomers and pharmaceutically acceptable salts thereof.

In certain embodiments the compounds of formula I according to the invention are those compounds wherein:

R$^1$ is phenyl optionally substituted by one or more substituents selected from the group consisting of Cl, F and $C_{1-7}$-haloalkyl or is morpholine or piperidine each of which is optionally substituted by OH;

R$^2$ is Br, I, $C_{1-7}$-haloalkoxy, $C_{3-6}$-cycloalkyl optionally substituted by phenyl, morpholine or piperidine; and R$^3$ is $C_{1-7}$-alkyl;

and optical isomers and pharmaceutically acceptable salts thereof.

In certain embodiments, the compounds of the invention are those compounds of formula I wherein R$^1$ is phenyl optionally substituted by one or more substituents selected from the group consisting of halogen and haloalkyl, for example, Cl, F and $C_{1-7}$-haloalkyl, for example the following compounds:

3-Methanesulfonyl-2-methyl-4-phenyl-6-trifluoromethoxy-quinoline;

6-Bromo-3-methanesulfonyl-2-methyl-4-phenyl-quinoline;

3-Methanesulfonyl-2-methyl-4-phenyl-6-piperidin-1-yl-quinoline;

3-Methanesulfonyl-2-methyl-6-morpholin-4-yl-4-phenyl-quinoline;

6-Bromo-4-(4-fluoro-phenyl)-3-methanesulfonyl-2-methyl-quinoline;

4-(4-Fluoro-phenyl)-3-methanesulfonyl-2-methyl-6-morpholin-4-yl-quinoline;

6-Bromo-4-(4-chloro-phenyl)-3-methanesulfonyl-2-methyl-quinoline;

4-(4-Chloro-phenyl)-3-methanesulfonyl-2-methyl-6-morpholin-4-yl-quinoline;

3-Methanesulfonyl-2-methyl-6-morpholin-4-yl-4-(4-trifluoromethyl-phenyl)-quinoline;
3-Methanesulfonyl-2-methyl-6-morpholin-4-yl-4-(2,4,5-trifluoro-phenyl)-quinoline;
6-Bromo-3-methanesulfonyl-2-methyl-4-(4-trifluoromethyl-phenyl)-quinoline; and
6-Bromo-3-methanesulfonyl-2-methyl-4-(2,4,5-trifluoro-phenyl)-quinoline.

Within this group, preferred compounds are those wherein $R^1$ is phenyl optionally substituted by halogen. Alternatively, preferred compounds are those within this group wherein $R^1$ is phenyl optionally substituted by haloalkyl.

In certain embodiments, the compounds of the invention are those compounds of formula I wherein $R^1$ is a 5 or 6 membered heterocycloalkyl group optionally substituted by OH. In particular, such compounds of the invention are those wherein $R^1$ is morpholine, for example the following compounds:
6-Iodo-3-methanesulfonyl-2-methyl-4-morpholin-4-yl-quinoline;
6-Bromo-3-methanesulfonyl-2-methyl-4-morpholin-4-yl-quinoline;
3-Methanesulfonyl-2-methyl-4-morpholin-4-yl-6-((1R,2R)-2-phenyl-cyclopropyl)-quinoline;
3-Methanesulfonyl-2-methyl-4-morpholin-4-yl-6-piperidin-1-yl-quinoline; and
6-Cyclopropyl-3-methanesulfonyl-2-methyl-4-morpholin-4-yl-quinoline.

Other such compounds of the invention are those compounds of formula I wherein $R^1$ is piperidine optionally substituted by OH, for example the following compounds:
6-Iodo-3-methanesulfonyl-2-methyl-4-piperidin-1-yl-quinoline;
1-(6-Iodo-3-methanesulfonyl-2-methyl-quinolin-4-yl)-piperidin-4-ol;
(R)-1-(6-Iodo-3-methanesulfonyl-2-methyl-quinolin-4-yl)-piperidin-3-ol; and
(S)-1-(6-Iodo-3-methanesulfonyl-2-methyl-quinolin-4-yl)-piperidin-3-ol.

In certain embodiments, compounds of the invention are those compounds of formula I wherein $R^2$ is Br, I, $C_{1-7}$-alkyl, $C_{1-7}$-alkoxy, $C_{1-7}$-haloalkyl, $C_{1-7}$-haloalkoxy. In particular, the invention provides those compounds wherein $R^2$ is Br. Alternatively, preferred compounds are those wherein $R^2$ is I. Further preferred, are those compounds wherein $R^2$ is $C_{1-7}$-alkyl.

In certain embodiments, the compounds of the invention are those in which $R^2$ is aryloxy or arylsulfonyl.

In other embodiments, compounds of the invention are those in which $R^2$ is $C_{3-6}$-cycloalkyl optionally substituted by phenyl. Separately considered are those compounds wherein the $C_{3-6}$cycloalkyl is unsubstituted and those in which the $C_{3-6}$-cycloalkyl is substituted by phenyl.

In certain embodiments, $R^2$ is —$NR^aR^b$ wherein $R^a$ and $R^b$ are each independently $C_{1-7}$-alkyl or $R^a$ and $R^b$, together with the nitrogen atom to which they are attached, form a 4 to 8 membered heterocycloalkyl group which is optionally substituted by one or more substituent(s) selected from the group consisting of halo, $C_{1-7}$-alkyl, $C_{1-7}$-alkoxy, hydroxy, phenyl and di($C_{1-7}$)alkylamino. In particular, preferred compounds are those in which $R^2$ is —$NR^aR^b$ and wherein $R^a$ and $R^b$ are each independently $C_{1-7}$-alkyl. Other preferred compounds are those in which $R^2$ is —$NR^aR^b$ and wherein $R^a$ and $R^b$, together with the nitrogen atom to which they are attached, form a 4 to 8 membered heterocycloalkyl group which is optionally substituted by one or more substituent(s) selected from the group consisting of halo, $C_{1-7}$-alkyl, $C_{1-7}$-alkoxy, hydroxy, phenyl and di($C_{1-7}$)alkylamino. Of this group, compounds wherein $R^2$ is piperidine are preferred. Also preferred are compounds of this group in which $R^2$ is morpholine.

The invention also encompasses the following novel intermediate compounds, which are useful in the preparation of the compounds of the invention:
(2-Amino-5-bromo-phenyl)-(4-trifluoromethyl-phenyl)-methanone;
(2-Amino-5-bromo-phenyl)-(2,4,5-trifluoro-phenyl)-methanone;
6-Bromo-2-methyl-4H-3,1-benzoxazin-4-one;
6-Iodo-2-methyl-4H-3,1-benzoxazin-4-one;
6-Bromo-3-methanesulfonyl-2-methyl-quinolin-4-ol;
6-Iodo-3-methanesulfonyl-2-methyl-quinolin-4-ol;
6-Bromo-4-chloro-3-methanesulfonyl-2-methyl-quinoline; and
4-Chloro-6-iodo-3-methanesulfonyl-2-methyl-quinoline.

Also encompassed by the invention are compounds of formula I having formulae I-a, I-b and I-c as follows:

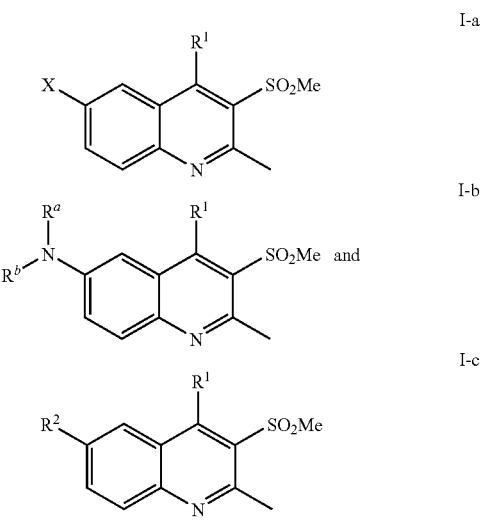

wherein
$R^1$ is a 5 or 6 membered heterocycloalkyl ring optionally substituted by OH, said heterocycloalkyl ring being preferably morpholine or piperidine,
$R^2$ is as defined hereinabove,
$R^a$ and $R^b$ are as defined hereinabove, and
X is Br or I.

The preparation of the intermediate compounds of the invention is described in the examples herein below.

The compounds of formula I-a, I-b and I-c can be manufactured by the following process of the invention comprising:
a) reacting a compound of formula IV

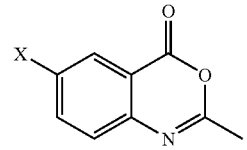

with MeCOCH$_2$SO$_2$Me to obtain a compound of formula V:

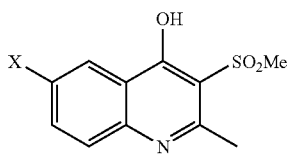

V b) reacting the compound of formula V with POCl$_3$ to obtain a compound of formula VI:

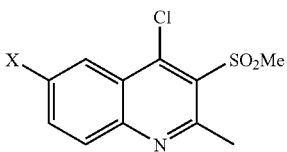

VI c) reacting the compound of formula VI with a compound of formula HR$^1$, to obtain a compound of formula I-a:

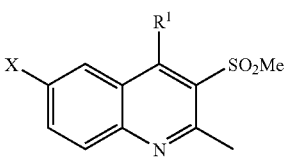

I-a and if desired, reacting the compound of formula I-a:
d) either with a compound of formula HNR$^a$R$^b$ to obtain a compound of formula I-b:

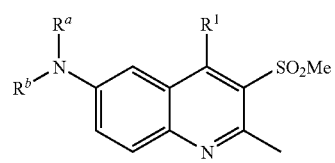

I-b or with a compound of formula R$^2$B(OH)$_2$ to obtain a compound of formula I-c:

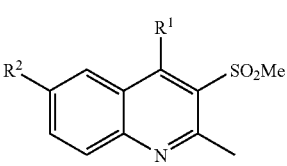

I-c wherein R$^1$ is a 5 or 6 membered heterocycloalkyl ring optionally substituted by OH, said heterocycloalkyl ring being preferably morpholine or piperidine,
R$^2$ is as defined hereinabove,
R$^a$ and R$^b$ are as defined hereinabove, and
X is Br or I, and if desired, converting the compound of formulae I-a, I-b or I-c obtained into a pharmaceutically acceptable salt. This process of manufacture is further detailed in scheme 4 hereinafter.

The following general schemes 1 to 3 further illustrate certain embodiments of the preparation of the compounds according to the invention. In these schemes, and unless otherwise stated, all starting materials, building blocks and intermediates are commercially available. All references cited are incorporated herein in their entirety.

In certain embodiments, the compounds of formula I wherein R$^3$ is methyl can be prepared according to the general method known in the art as described with scheme 1:

Scheme 1:

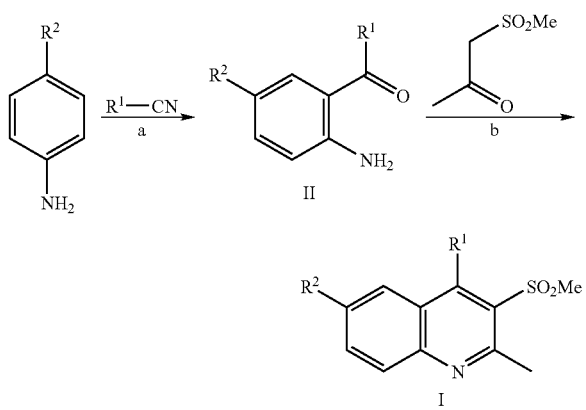

a) 1. GaCl$_3$ (1.2 eq), BCl$_3$ (1.1 eq), DCE, reflux, 12 h; 2. H$_2$O, 60°, 0.5 h
b) NaAuCl$_4$ (2.5 mol %), iPrOH, reflux, 2-4 d Step a: This step can be performed following a procedure developed by T. Sugasawa, T. Toyoda, M. Adachi, and K. Sasakura, J. Am. Chem. Soc. 100, 4842-4852 (1978) and improved by A. W. Douglas, N. L. Abramson, I. N. Houpis, S. Karady, A. Molina, L. C. Xavier, N. Yasuda, Tetrahedron Lett. 35, 6807-6810 (1994).

Step b: This step can be conducted according to the procedure developed by A. Arcadi, M. Chiarini, S. Di Giuseppe, and F. Marinelli, Synlett 203-206 (2003) for 1,3-diketones and β-ketoesters and was extended to the reaction with β-ketoamides and β-ketosulfones. The latter were prepared by heating intermediates of formula II for several days with about 2 equivalents of methylsulfonyl acetone. The regioisomer shown below is also formed in 5-10% yield.

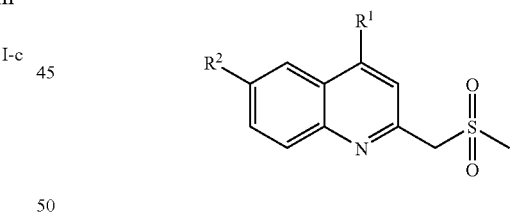

In certain embodiments, the compounds of formula I wherein R$^3$ is methyl can be prepared according to the general method known in the art as described in scheme 2 herein below:

Scheme 2:

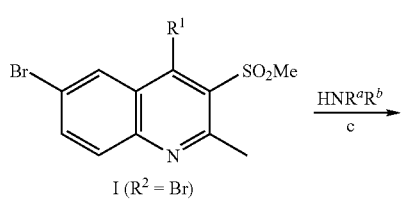

I (R$^2$ = Br)

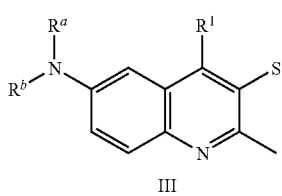

c) HNR$^a$R$^b$ (1.2 eq), Pd$_2$(dba)$_3$ + X-PHOS (0.02 eq), Cs$_2$CO$_3$ (1.5 eq), t-BuOH, 110°, 2 h Step c: This step can be performed following a methodology developed by J. P. Wolfe and S. L. Buchwald (J. Org. Chem. 2000, 65, 1144-1157). X-PHOS was shown to be superior to BINAP as a catalyst. Preferred solvent was tert.-butanol alone or as mixture with dioxane.

In certain embodiments, the compounds of formula I wherein R$^3$ is methyl can be prepared according to the general method of the invention as described in scheme 3 herein below:

Scheme 3:

d) Ac$_2$O, neat, 100°, 1 h
e) MeCOCH$_2$SO$_2$Me, t-BuOK (2 eq), DMF, 100°, 0.5 h
f) POCl$_3$ (1.1 eq), Me$_2$NTol (2 eq), toluene, 110°, 7 h
g) HR$^1$ (1.2 eq), DIPEA (1.2 eq), DMF, 100°, 30 min.
h) HNR$^a$R$^b$ (1.2 eq), Pd$_2$(dba)$_3$ + X-PHOS (0.02 eq), t-BuOH, Cs$_2$CO$_3$ (1.5 eq), 110°, 2 h
i) R$^2$B(OH)$_2$ (2 eq), K$_3$PO$_4$ (4 eq), Pd(TPP)$_4$ (0.03 eq), dioxane, reflux, 8 h In this scheme:
R$^1$ is a 5 or 6 membered heterocycloalkyl ring optionally substituted by OH, said heterocycloalkyl ring being preferably morpholine or piperidine.
R$^2$ is as defined hereinabove.
R$^a$ and R$^b$ are as defined hereinabove.
X is Br or I.

Step d: This step can be performed following a procedure developed J. B. Jiang, D. P. Hesson, B. A. Dusak, D. L. Dexter, G. J. Kang, E. Hamel, J. Med. Chem. 1990, 33, 1721-1728.

Step e: This step can be a one-pot transformation under anhydrous basic conditions with e.g. 2 equivalents of sodium hydride or potassium tert.-butylate in N'N-dimethylformamide which involves the elimination of potassium acetate. No chromatography is needed.

Step f: This step is an optimized procedure for the formation of the vinylogous sulfonyl chloride with e.g. 2 equivalents of the stable base N'N-dimethyl-toluidine and one equivalent of phosphorous oxy chloride in toluene at reflux for about 6-9 h. The reaction can also be performed in neat phosphorous oxychloride at reflux for about 0.5-1 h with one equivalent of N,N-diethylaniline as base. The product can be directly precipitated and isolated without chromatography.

Step g: This step can proceed either by nucleophilic substitution with primary and secondary amines in the appropriate solvent, e.g. N'N-dimethylformamide, or by reaction under Buchwald conditions (method c)

Step h: This step is a reaction under Buchwald conditions (method c).

Step i: Substrates of formula VII (where R$^2$=Br) reacted smoothly under Suzuki cross-coupling conditions with a base, e.g. tribasic potassium phosphate as in the appropriate solvent, e.g. dioxane at reflux.

The preparation of compounds of formula I is further described in detail in working examples 1-21.

As mentioned earlier, the compounds of formula I and their pharmaceutically acceptable addition salts possess valuable pharmacological properties. The compounds of the present invention have an affinity to the GABA$_B$ receptor.

The compounds were investigated in accordance with the tests given hereinafter.

Intracellular Ca$^{2+}$ Mobilization Assay

Chinese Hamster Ovary (CHO) cells stably expressing human GABA$_B$R1aR2a and Gα16 were seeded at 5×10$^4$ cells/well in the poly-D-lysine treated, 96-well, black/clear-bottomed plates (BD Biosciences, Palo Alto, Calif.). 24 h later, the cells were loaded for 90 min at 37° C. with 4 μM Flou-4 acetoxymethyl ester (Catalog No. F-14202, Molecular Probes, Eugene, Oreg.) in loading buffer (1×HBSS, 20 mM HEPES, 2.5 mM Probenecid). Hanks' Balanced Salt Solution (HBSS) (10×) (catalog No. 14065-049) and HEPES (1M) (catalog No. 15630-056) were purchased from Invitrogen, Carlsbad, Calif. Probenecid (250 mM) (catalog No. P8761) was from Sigma, Buchs, Switzerland. The cells were washed five times with loading buffer to remove excess dye and intracellular calcium mobilization, $[Ca^{2+}]$ was measured using a Fluorometric Imaging Plate Reader (FLIPR, Molecular Devices, Menlo Park, Calif.) as described previously (Porter et al., Br. J. Pharmacol., 128, 13-20, 1999). The enhancers were applied 15 min before the application of the GABA. For GABA shift assay, concentration-response curves of GABA (0.0003-30 µM) were determined in the absence and presence of 10 µM enhancer. The GABA-shift is defined as Log [$EC_{50}$ (GABA+10 µM enhancer)/$EC_{50}$ (GABA alone)]. The % maximum enhancing effect (% $E_{max}$) and potency ($EC_{50}$ value) of each enhancer was determined from concentration-response curve of the enhancer (0.001-30 µM) in the presence of 10 nM GABA ($EC_{10}$). Responses were measured as peak increase in fluorescence minus basal, normalized to the maximal stimulatory effect induced by 10 µM GABA alone (considered 100%) and 10 nM GABA alone (considered 0%). The data were fitted with the equation $Y=100+(Max-100)/(1+(EC_{50}/[drug])^n)$ where Max is the maximum effect, $EC_{50}$ the concentration eliciting a half-maximum effect and n the Hill slope.

| | Intracellular $Ca^{2+}$mobilization Assay in CHO-$GABA_B$R1aR2a-Gα16 cell | | GABA shift |
|---|---|---|---|
| Example | $E_{max}$ (%) at 10 nM GABA alone = 0% 10 µM GABA alone = 100% | $EC_{50}$ (µM) at 10 nM GABA | Log [$EC_{50}$(GABA + 10 µM cp)/ $EC_{50}$(GABA alone)] |
| 1 | 56 | 0.85 | −0.7 |
| 5 | 30 | 2.1 | −0.4 |
| 9 | 48 | 0.6 | −1.2 |
| 11 | 26 | 0.8 | −0.8 |
| 14 | 37 | 2.1 | −0.45 |

The present invention also provides pharmaceutical compositions containing one or more compounds of the invention, for example compounds of formula I and their pharmaceutically acceptable salts and a pharmaceutically acceptable carrier. Such pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parentally, e.g. in the form of injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic and organic excipients. Lactose, corn starch or derivatives thereof, talc, stearic acid or its salts etc can be used as such excipients e.g. for tablets, dragées and hard gelatine capsules. Suitable excipients for soft gelatine capsules are e.g. vegetable oils, waxes, fats, semi-solid and liquid polyols. Suitable excipients for the manufacture of solutions and syrups include but are not limited to water, polyols, saccharose, invert sugar, glucose. Suitable excipients for injection solutions include but are not limited to water, alcohols, polyols, glycerol, vegetable oils. Suitable excipients for suppositories include but are not limited to natural or hardened oils, waxes, fats, semi-liquid or liquid polyols.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substance into a galenical administration form together with one or more therapeutically inert carriers.

Compounds of formula I are active on the $GABA_B$ receptor. Thus, the invention provides a method for the treatment of CNS disorders, such as anxiety, depression, epilepsy, schizophrenia, cognitive disorders, spasticity and skeletal muscle rigidity, spinal cord injury, multiple sclerosis, amyotrophic lateral sclerosis (ALS), cerebral palsy, neuropathic pain and craving associated with cocaine and nicotine, psychosis, panic disorder, post traumatic stress disorders and gastrointestinal disorders.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

| | | Tablet Formulation (Wet Granulation) mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| | | Capsule Formulation mg/capsule | | | |
|---|---|---|---|---|---|
| Item | Ingredients | 5 mg | 20 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

EXAMPLES

Synthesis of Intermediates

Examples A.1 to A.4

Intermediates of Formula II

Example A.1

(2-Amino-5-bromo-phenyl)-(4-fluoro-phenyl)-methanone

In a reactor fitted with magnetic stir bar, rubber septum, thermometer, Hickmann-condenser, nitrogen-inlet and nitrogen-outlet connected to a washing bottle containing 30% NaOH, anhydrous beads of gallium (III) chloride (11.7 g, 66 mmol) were added at once and then dissolved by the addition of 1,2-dichloroethane (100 mL). This solution was cooled in ice, then 4-bromoaniline (9.5 g, 55 mmol) was added slowly while keeping the temperature below 5° C. Then the solution was cooled to −10° C., and a fresh 1 M solution of boron trichloride in dichloromethane (61 ml) was added via a syringe fitted with a teflon stop-cock while keeping the temperature below −5° C. Finally, 4-fluorobenzonitrile (6.7 g, 55 mmol) was added, and the mixture was allowed to warm to 20° C. The Hickmann-condenser was replaced by a normal reflux condenser, and the reaction mixture was heated in an oil-bath (90° C.) over 1-2 h in order to distill off all the dichloromethane (a total of ca. 100 mL of distillate was collected) until the reflux temperature of 80° C. was achieved. Refluxing was continued for 14 h. The reaction mixture was cooled in ice and hydrolyzed slowly with water (100 mL) and then heated at 60-80° C. for 20-30 min. in order to hydrolyze the imine. The reaction mixture was cooled again and then extracted twice with dichloromethane and water. The crude product was purified by chromatography with a heptane/ethyl acetate gradient from 100:0 to 80:20 to give a yellow solid (7 g, 43%). MS: m/z=294 (M).

Example A.2

(2-Amino-5-bromo-phenyl)-(4-chloro-phenyl)-methanone

The title compound was prepared by reacting 4-bromoaniline and 4-chlorobenzonitrile following to the procedure of example A.1. Yield 33%; MS: m/z=310 (M).

Example A.3

(2-Amino-5-bromo-phenyl)-(4-trifluoromethyl-phenyl)-methanone

The title compound was prepared by reacting 4-bromoaniline and 4-(trifluoromethyl)benzonitrile following to the procedure of example A.1. Yield 34%; MS: m/z=344 (M).

Example A.4

(2-Amino-5-bromo-phenyl)-(2,4,5-trifluoro-phenyl)-methanone

The title compound was prepared by reacting 4-bromoaniline and 2,4,5-trifluorobenzonitrile following to the procedure of example A.1. Yield 26%; MS: m/z=330 (M).

Examples B.1 and B.2

Intermediates of Formula IV

Example B.1

6-Bromo-2-methyl-4H-3,1-benzoxazin-4-one

2-Amino-5-bromobenzoic acid (25 g, 116 mmol) was added in portions to acetic anhydride (150 mL) giving a slightly exothermic reaction to 30° C. The suspension was heated at reflux for 2 h. The product crystallized spontaneously upon cooling. After stirring in ice for 30 min, the crystals were filtered off and washed twice with heptane. The crystals were thoroughly dried at 0.1 mbar/50° C. One obtained 22.4 g (85%) of beige crystals. MS: m/z=239/241 (M).

Example B.2

6-Iodo-2-methyl-4H-3,1-benzoxazin-4-one

2-Amino-5-iodobenzoic acid (25.4 g, 96.6 mmol) was added in portions to cold acetic anhydride (100 mL). The suspension was first stirred without cooling, then the resulting thick precipitate was heated at reflux for 1 h (red solution). The product crystallized spontaneously upon cooling. After stirring in ice for 30 min, the crystals were filtered off and washed twice with heptane. The crystals were thoroughly dried at 0.1 mbar/50° C. One obtained 25.1 g (90%) of beige crystals. MS: m/z=287 (M).

Examples C.1 and C.2

Intermediates of Formula V

Example C.1

6-Bromo-3-methanesulfonyl-2-methyl-quinolin-4-ol

Methanesulfonylacetone (12.6 g, 92.9 mmol) was dissolved in N,N-dimethylformamide (200 mL) and cooled in ice under nitrogen. Then potassium tert.butylate (11.7 g, 102 mmol) was added (exothermic 20° C.) and stirring without cooling continued for 15 min. Cooled in ice again, then 6-bromo-2-methyl-4H-3,1-benzoxazin-4-one (example B.1) (22.3 g, 92.9 mmol) was added and then stirred without cooling for 4 h. Cooled in ice again, then potassium tert.butylate (11.7 g, 102 mmol) was added, and the resulting red solution was stirred at 20° C. for 15 min and then heated at 100° C. for 30 min. After cooling, 4 M HCl (30 mL) was added, and the mixture was evaporated thoroughly at 0.1 mbar/50° C. The residue was suspended in water (200 mL) and stirred vigorously for 30 min which led to the formation of a filterable precipitate. This solid was filtered off and washed with water (50 mL). One obtained 14.25 g (48.5%) of white crystals. MS: m/z=315/317 (M+H).

Example C.2

6-Iodo-3-methanesulfonyl-2-methyl-quinolin-4-ol

Methanesulfonylacetone (13 g, 95 mmol) was dissolved in N,N-dimethylformamide (200 mL) and cooled in ice under nitrogen. Then potassium tert.butylate (11.2 g, 100 mmol) was added (exothermic, 20° C.) and stirring without cooling continued for 15 min. Cooled in ice again, then 6-bromo-2- methyl-4H-3,1-benzoxazin-4-one (example B.2) (27.4 g, 95.4 mmol) was added and then stirred without cooling for 4 h. Cooled in ice again, then potassium tert.butylate (11.2 g, 100 mmol) was added and the resulting red solution was stirred at 20° C. for 15 min and then heated at 100° C. for 30 min. After cooling, 4 M HCl (30 mL) was added, and the mixture was evaporated thoroughly at 0.1 mbar/50° C. The residue was suspended in water (200 mL) and stirred vigorously for 30 min which led to the formation of a filterable precipitate. This solid was filtered off and washed with water (50 mL). The crude product was heated to reflux in MeOH (60 mL) in order to dissolve mainly impurities. The suspension was allowed to cool to 20° C. again, and the solid was filtered off. One obtained 15.1 g (43%) of a white solid. MS: m/z=363 (M).

Examples D.1 and D.2

Intermediates of Formula VI

Example D.1

6-Bromo-4-chloro-3-methanesulfonyl-2-methyl-quinoline

6-Bromo-3-methanesulfonyl-2-methyl-quinolin-4-ol (example C.1) (6 g, 19 mmol) and N,N-dimethyl-p-toluidine (5.5 mL, 38 mmol) were dissolved in toluene (60 mL) and heated under argon to reflux. The phosphorous oxychloride (1.9 mL, 20.9 mL) was added and heating at reflux continued for 6.5 h. The product precipitated spontaneously upon cooling to 20° C., the crystals were filtered off and washed with little toluene. One obtained 4.19 g (66%) of light brown crystals. Since the product is somewhat soluble in toluene, the mother liquor was extracted with 3 N HCl (2×), sat. NaCl (2×). The residue was purified by chromatography on silica gel in dichloromethane. One obtained 1.17 g (18%) of additional material. MS: m/z=333/335 (M).

Example D.2

4-Chloro-6-iodo-3-methanesulfonyl-2-methyl-quinoline

6-Iodo-3-methanesulfonyl-2-methyl-quinolin-4-ol (example C.2) (14.7 g, 40.5 mmol) and N,N-dimethyl-p-toluidine (11.7 mL, 81 mmol) were dissolved in toluene (150 mL) and heated under argon to reflux. Then phosphorous oxychloride (4.1 mL, 44.5 mmol) was added and heating at reflux continued for 9.5 h. The thick suspension became gradually a dark solution. The reaction mixture was allowed to cool and then extracted with dichloromethane (not soluble in toluene), cold 1 N HCl (2×), and sat. NaCl (2×). The product was crystallized from heptane/dichloromethane. One obtained 12 g (78%) of white crystals. MS: m/z=381 (M).

Synthesis of the Compounds of Formula I According to the Invention

In the following examples, unless otherwise specified, all the starting materials are commercially available.

Example 1

3-Methanesulfonyl-2-methyl-4-phenyl-6-trifluoromethoxy-quinoline (2-Amino-5-trifluoromethoxy-phenyl)-phenyl-methanone (0.3 g, 1 mmol), methylsulfonylacetone (0.22 g, 2 mmol) and sodium tetrachloroaurate (III) dihydrate (13 mg, 0.036 mmol) were mixed in 2-propanol (3 mL) and heated at reflux under nitrogen for 5 days. 2-propanol was evaporated and the residue was purified by flash chromatography on silica gel in heptane/ethyl acetate 2:1. One obtained 154 mg (34%) of a white solid. MS: m/z=382 (M+H).

Example 2

6-Bromo-3-methanesulfonyl-2-methyl-4-phenyl-quinoline (2-Amino-5-bromo-phenyl)-phenyl-methanone (10 g, 36 mmol), methanesulfonylacetone (7.4 g, 54 mmol) and sodium tetrachloroaureate(III) dihydrate (720 mg, 1.8 mmol) were heated at reflux in 2-propanol (100 mL) for 4.5 days. The resulting suspension was evaporated to dryness and the residue extracted with dichloromethane (2×), 1 N NaOH (2×), which removes excess of methanesulfonylacetone, and sat. NaCl (1×). The crude product was purified twice by chromatography in dichloromethane and then crystallized from dichloromethane/heptane by evaporation of dichloromethane. One obtained 4.6 g (33%) of beige crystals. MS: m/z=375/377 (M).

Example 3

3-Methanesulfonyl-2-methyl-4-phenyl-6-piperidin-1-yl-quinoline

A tube placed under argon was charged with tris(dibenzylideneacetone)dipalladium chloroform complex (3 mg), rac-2,2'-bis(diphenylphosphino)-1,1'-binaphthyl (3 mg) and cesium carbonate (121 mg, 0.37 mmol). 6-Bromo-3-methanesulfonyl-2-methyl-4-phenyl-quinoline (compound of example 2) (100 mg, 0.26 mmol) in dioxane/tert.-butanol 1:1 (15 ml) was added, followed by piperidine (0.027 ml, 0.031 mmol). The tube was sealed and heated at 120° C. for 2 h. The reaction mixture was cooled to 20° C., diluted with heptane, filtered through dicalite and purified directly by flash chromatography on silica gel in heptane/ethyl acetate 40:60 to give a yellow solid (47 mg, 46%). MS: m/z=381 (M+H).

Example 4

3-Methanesulfonyl-2-methyl-6-morpholin-4-yl-4-phenyl-quinoline

A tube placed under argon was charged with tris(dibenzylideneacetone)dipalladium chloroform complex (55 mg, 0.053 mmol), 2-dicyclohexylphosphino-2',4',6'-triisopropyl-biphenyl (63 mg, 0.106 mmol) and cesium carbonate (1.3 g, 3.99 mmol). 6-Bromo-3-methanesulfonyl-2-methyl-4-phenyl-quinoline (compound of example 2) (1 g, 2.66 mmol) in tert.-butanol (20 ml) was added, followed by morpholine (0.28 g, 3.19 mmol). The tube was sealed and heated at 110° C. for 2 h. The reaction mixture was cooled to 20° C., diluted with heptane, filtered through dicalite and purified directly by flash chromatography on silica gel in heptane/ethyl acetate 80:20 to give a yellow solid (800 mg, 78%). MS: m/z=383 (M+H).

Example 5

6-Iodo-3-methanesulfonyl-2-methyl-4-morpholin-4-yl-quinoline

4-Chloro-6-iodo-3-methanesulfonyl-2-methyl-quinoline (compound of example D.2) (1 g, 2.62 mmol), morpholine (274 mg, 3.1 mmol) and N,N-diisopropyl ethyl amine (406 mg, 3.1 mmol) were heated at 100° C. in dry N,N-dimethylformamide (10 mL) for 30 min. The reaction mixture was evaporated to dryness, and the residue extracted with dichloromethane, 10% $Na_2CO_3$ and sat. NaCl. The crude product was purified by chromatography on silica gel in dichloromethane/ethyl acetate 5:1. One obtained 913 mg (80%) of a yellow foam. MS: m/z=433 (M+H).

Example 6

6-Bromo-3-methanesulfonyl-2-methyl-4-morpholin-4-yl-quinoline

6-Bromo-4-chloro-3-methanesulfonyl-2-methyl-quinoline (compound of example D.1) (11.5 g, 34.4 mmol), morpholine (3.3 mL, 37.8 mmol) and N,N-diisopropyl ethyl amine (6.5 mL, 37.8 mmol) were heated at 100° C. in dry N,N-dimethylformamide (10 mL) for 30 min. The reaction mixture was evaporated to dryness, and the residue extracted with dichloromethane, 10% $Na_2CO_3$ and sat. NaCl. The crude product was stirred and heated at 80° C. in ethyl acetate (80 mL) for 10 min, the resulting suspension was cooled in ice, the crystals were filtered off and washed with little cold ethyl acetate. One obtained 10.8 g (81%) of white crystals. MS: m/z=385/387 (M+H).

Example 7

3-Methanesulfonyl-2-methyl-4-morpholin-4-yl-6-((1R,2R)-2-phenyl-cyclopropyl)-quinoline 6-Bromo-3-methanesulfonyl-2-methyl-4-morpholin-4-yl-quinoline (compound of example 6) (300 mg, 0.78 mmol), trans-2-phenylcyclopropylboronic acid (189 mg, 1.17 mmol), potassium phosphate (496 mg, 2.33 mmol) and tetrakis(triphenylphosphine)-palladium (27 mg, 0.023 mmol) were heated at reflux under argon for 8 h. The crude product was purified by chromatography on silica gel in dichloromethane/ethyl acetate 5:1 with a gradient from 100:0 to 80:20. One obtained 202 mg (60%) of white crystals. MS: m/z=423 (M+H).

Example 8

3-Methanesulfonyl-2-methyl-4-morpholin-4-yl-6-piperidin-1-yl-quinoline

A tube placed under argon was charged with tris(dibenzylideneacetone)dipalladium chloroform complex (11 mg, 0.010 mmol), 2-dicyclohexylphosphino-2',4',6'-triisopropylbiphenyl (10 mg, 0.021 mmol) and cesium carbonate (1.3 g, 3.99 mmol). 6-Bromo-3-methanesulfonyl-2-methyl-4-morpholin-4-yl-quinoline (compound of example 6) (200 mg, 0.52 mmol) in tert.-butanol (10 ml) was added, followed by piperidine (0.053 g, 0.62 mmol). The tube was sealed and heated at 110° C. for 2 h. The reaction mixture was cooled to 20° C., diluted with heptane, filtered through dicalite and purified directly by flash chromatography on silica gel in heptane/ethyl acetate 80:20 to give a yellow solid (160 mg, 79%). MS: m/z=390 (M+H).

Example 9

6-Iodo-3-methanesulfonyl-2-methyl-4-piperidin-1-yl-quinoline

4-Chloro-6-iodo-3-methanesulfonyl-2-methyl-quinoline (compound of example D.2) (300 mg, 0.786 mmol), piperidine (74 mg, 0.865 mmol) and N,N-diisopropyl ethyl amine (0.148 mL, 0.865 mmol) were heated in dry N,N-dimethylformamide (3 mL) for 4 h at 100° C. N,N-Dimethylformamide was evaporated at 40° C./0.1 mbar, and the residue directly purified by chromatography on silica gel in dichloromethane. One obtained 184 mg (54%) of white crystals. MS: m/z=431 (M+H).

Example 10

1-(6-Iodo-3-methanesulfonyl-2-methyl-quinolin-4-yl)-piperidin-4-ol

4-Chloro-6-iodo-3-methanesulfonyl-2-methyl-quinoline (compound of example D.2) (300 mg, 0.786 mmol), 4-hydroxypiperidine (87 mg, 0.865 mmol) and N,N-diisopropyl ethyl amine (0.148 mL, 0.865 mmol) were heated in dry N,N-dimethylformamide (3 mL) for 0.5 h at 100° C. N,N-Dimethylformamide was evaporated at 40° C./0.1 mbar, and the residue directly purified by chromatography on silica gel in dichloromethane/methanol 20:1. One obtained a yellow oil which was triturated with ethyl acetate and the resulting white crystals were filtered off. One obtained 218 mg (62%) of white crystals. MS: m/z=447 (M+H).

Example 11

(R)-1-(6-Iodo-3-methanesulfonyl-2-methyl-quinolin-4-yl)-piperidin-3-ol

4-Chloro-6-iodo-3-methanesulfonyl-2-methyl-quinoline (compound of example D.2) (300 mg, 0.786 mmol), (R)-(+)-3-hydroxypiperidine (119 mg, 0.865 mmol) and N,N-diisopropyl ethyl amine (0.148 mL, 0.865 mmol) were heated in dry N,N-dimethylformamide (3 mL) for 0.5 h at 100° C. N,N-Dimethylformamide was evaporated at 40° C./0.1 mbar, the residue was extracted with dichloromethane and 10% $Na_2CO_3$, and then purified by chromatography on silica gel in dichloromethane/methanol 20:1. One obtained a yellow oil which was triturated with ethyl acetate and the resulting white crystals were filtered off. One obtained 209 mg (60%) of white crystals. MS: m/z=447 (M+H).

Example 12

(S)-1-(6-Iodo-3-methanesulfonyl-2-methyl-quinolin-4-yl)-piperidin-3-ol

4-Chloro-6-iodo-3-methanesulfonyl-2-methyl-quinoline (compound of example D.2) (300 mg, 0.786 mmol), (S)-(+)-3-hydroxypiperidine (119 mg, 0.865 mmol) and N,N-diisopropyl ethyl amine (0.148 mL, 0.865 mmol) were heated in dry N,N-dimethylformamide (3 mL) for 0.5 h at 100° C. N,N-Dimethylformamide was evaporated at 40° C./0.1 mbar, the residue was extraced with dichloromethane and 10% $Na_2CO_3$, and then purified by chromatography on silica gel in dichloromethane/methanol 20:1. One obtained a yellow oil which was triturated with ethyl acetate, and the resulting white crystals were filtered off. One obtained 191 mg (54%) of white crystals. MS: m/z=447 (M+H).

Example 13

6-Cyclopropyl-3-methanesulfonyl-2-methyl-4-morpholin-4-yl-quinoline

6-Bromo-3-methanesulfonyl-2-methyl-4-morpholin-4-yl-quinoline (compound of example 6) (0.5 g, 1.3 mmol), cyclopropylboronic acid (0.167 g, 1.95 mmol), potassium phosphate tribasic (0.826 g, 3.89 mmol) and tetrakis(triphenylphosphine)palladium(0) (45 mg, 0.039) were mixed together in dioxane (7 mL) and heated at reflux under argon for 8 h. After extraction with dichloromethane and half-saturated NaCl solution, the crude product was purified chromatography on silica gel in dichloromethane/ethyl acetate with a gradient from 100:0 to 90:10. One obtained 0.1 g (21%) of white crystals. MS: m/z=347 (M+H).

Example 14

6-Bromo-4-(4-fluoro-phenyl)-3-methanesulfonyl-2-methyl-quinoline (2-Amino-5-bromo-phenyl)-(4-fluoro-phenyl)-methanone (compound of example A.1) (4 g, 14 mmol), methanesulfonylacetone (2.78 g, 20 mmol) and sodium tetrachloroaureate(III) dihydrate (0.27 g, 0.7 mmol) were heated at reflux in 2-propanol (50 ml) for 4 days. The resulting mixture was evaporated to dryness and the residue extracted with dichloromethane (2×), 1 N NaOH (2×) and NaCl (1×). The crude product was purified by chromatography in heptane/ethyl acetate with a gradient from 100:0 to 70:30. One obtained a light brown solid (1.5 g, 28%). MS: m/z=394 (M).

Example 15

4-(4-Fluoro-phenyl)-3-methanesulfonyl-2-methyl-6-morpholin-4-yl-quinoline

A tube placed under argon was charged with tris(dibenzylideneacetone)dipalladium chloroform complex (79 mg, 0.076 mmol), 2-dicyclohexylphosphino-2',4',6'-triisopropyl-biphenyl (73 mg, 0.152 mmol) and cesium carbonate (1.86 g, 5.7 mmol). 6-Bromo-4-(4-fluoro-phenyl)-3-methanesulfonyl-2-methyl-quinoline (compound of example 14) (200 mg, 0.52 mmol) in tert.-butanol (20 ml) was added, followed by morpholine (0.40 g, 4.56 mmol). The tube was sealed and heated at 110° C. for 2 h. The reaction mixture was cooled to 20° C., diluted with heptane, filtered through dicalite and purified directly by flash chromatography on silica gel in heptane/ethyl acetate with a gradient from 100:0 to 40:60 to give a yellow solid (850 mg, 56%). MS: m/z=401 (M+H).

Example 16

6-Bromo-4-(4-chloro-phenyl)-3-methanesulfonyl-2-methyl-quinoline (2-Amino-5-bromo-phenyl)-(4-chloro-phenyl)-methanone (compound of example A.2) (4 g, 12.9 mmol), methanesulfonylacetone (2.63 g, 19.3 mmol) and sodium tetrachloroaureate(III) dihydrate (0.26 g, 0.64 mmol) were heated at reflux in 2-propanol (50 ml) for 4 days. The resulting mixture was evaporated to dryness and the residue extracted with dichloromethane (2×), 1 N NaOH (2×) and sat. NaCl (1×). The crude product was purified by chromatography on silica gel in dichloromethane. The product was crystallized from dichloromethane/heptane by evaporation of dichloromethane. One obtained a light yellow solid (1 g, 19%). MS: m/z=410 (M).

Example 17

4-(4-Chloro-phenyl)-3-methanesulfonyl-2-methyl-6-morpholin-4-yl-quinoline

A tube placed under argon was charged with tris(dibenzylideneacetone)dipalladium chloroform complex (40 mg, 0.039 mmol), 2-dicyclohexylphosphino-2',4',6'-triisopropyl-biphenyl (37 mg, 0.078 mmol) and cesium carbonate (952 mg, 2.92 mmol). 6-Bromo-4-(4-chloro-phenyl)-3-methanesulfonyl-2-methyl-quinoline (compound of example 16) (800 mg, 1.95 mmol) in tert.-butanol (20 ml) was added, followed by morpholine (0.204 g, 2.33 mmol). The tube was sealed and heated at 110° C. for 2 h. The reaction mixture was cooled to 20° C., diluted with heptane, filtered through dicalite and purified directly by flash chromatography on silica gel in heptane/ethyl acetate with a gradient 100:0 to 40:60 to give a yellow solid (350 mg, 43%). MS: m/z=417 (M+H).

Example 18

3-Methanesulfonyl-2-methyl-6-morpholin-4-yl-4-(4-trifluoromethyl-phenyl)-quinoline A tube placed under argon was charged with tris(dibenzylideneacetone)dipalladium chloroform complex (51 mg, 0.05 mmol), 2-dicyclohexylphosphino-2',4',6'-triisopropyl-biphenyl (47 mg, 0.10 mmol) and cesium carbonate (1.21 g, 3.71 mmol). 6-Bromo-3-methanesulfonyl-2-methyl-4-(4-trifluoromethyl-phenyl)-quinoline (compound of example 20) (800 mg, 1.95 mmol) in tert.-butanol (20 ml) was added, followed by morpholine (0.259 g, 2.97 mmol). The tube was sealed and heated at 110° C. for 2 h. The reaction mixture was cooled to 20° C., diluted with heptane, filtered through dicalite and purified directly by flash chromatography on silica gel in heptane/ethyl acetate with a gradient 100:0 to 40:60 to give a yellow solid (320 mg, 29%). MS: m/z=451 (M+H).

Example 19

3-Methanesulfonyl-2-methyl-6-morpholin-4-yl-4-(2,4,5-trifluoro-phenyl)-quinoline A tube placed under argon was charged with tris(dibenzylideneacetone)dipalladium chloroform complex (19 mg, 0.019 mmol), 2-dicyclohexylphosphino-2',4',6'-triisopropyl-biphenyl (18 mg, 0.019 mmol) and cesium carbonate (454 mg, 1.4 mmol). 6-Bromo-3-methanesulfonyl-2-methyl-4-(2,4,5-trifluoro-phenyl)-quinoline (compound of example 21) (400 mg, 0.93 mmol) in tert.-butanol (20 ml) was added, followed by morpholine (97 mg, 1.11 mmol). The tube was sealed and heated at 110° C. for 2 h. The reaction mixture was cooled to 20° C., diluted with heptane, filtered through dicalite and purified directly by flash chromatography on silica gel in heptane/ethyl acetate with a gradient 100:0 to 40:60 to give a yellow solid (250 mg, 62%). MS: m/z=437 (M+H).

Example 20

6-Bromo-3-methanesulfonyl-2-methyl-4-(4-trifluoromethyl-phenyl)-quinoline (2-Amino-5-bromo-phenyl)-(4-trifluoromethyl-phenyl)-methanone (compound of example A.3) (4 g, 11.6 mmol), methanesulfonylacetone (2.37 g, 17.4 mmol) and sodium tetrachloroaureate(III) dihydrate (0.23 g, 0.58 mmol) were heated at reflux in ethanol (50 ml) for 4 days. The resulting mixture was evaporated to dryness and the residue extracted with dichloromethane (2×), NaOH (2×) and NaCl (1×). The crude product was purified by chromatography on silica gel in heptane/ethyl acetate 70:30. One obtained a light yellow solid (1.5 g, 29%). MS: m/z=444 (M).

Example 21

6-Bromo-3-methanesulfonyl-2-methyl-4-(2,4,5-trifluoro-phenyl)-quinoline (2-Amino-5-bromo-phenyl)-(2,4,5-trifluoro-phenyl)-methanone (compound of example A.4) (1.9 g, 5.7 mmol), methanesulfonylacetone (1.18 g, 8.6 mmol) and sodium tetrachloroaureate(III) dihydrate (0.12 g, 0.28 mmol) were heated at reflux in 2-propanol (50 ml) for 4 days. The resulting mixture was evaporated to dryness and the residue extracted with dichloromethane (2×), NaOH (2×) and NaCl (1×). The crude product was purified by chromatography on silica gel with a heptane/ethyl acetate gradient from 100:0 to 90:10. One obtained a light yellow solid (0.5 g, 20%). MS: m/z=430 (M).

The invention claimed is:
1. A compound of formula I:

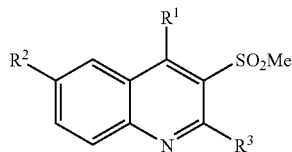

wherein
R$^1$ is phenyl optionally substituted by one or more substituents selected from the group consisting of Cl, F, C$_{1-7}$-haloalkyl, hydroxy, C$_{1-7}$-alkoxy, C$_{1-7}$-haloalkoxy, di(C$_{1-7}$)alkylamino and C$_{1-7}$-alkylsulfonyl,
or is 5 or 6 membered heterocycloalkyl optionally substituted by OH;
R$^2$ is Br, I, C$_{1-7}$-alkyl, C$_{1-7}$ alkoxy, C$_{1-7}$-haloalkyl, C$_{1-7}$-haloalkoxy, aryloxy, arylsulfonyl, C$_{3-6}$-cycloalkyl optionally substituted by phenyl, or NR$^a$R$^b$ wherein R$^a$ and R$^b$ are each independently C$_{1-7}$-alkyl, or R$^a$ and R$^b$, together with the nitrogen atom to which they are attached, form a 4 to 8 membered heterocycloalkyl group which is optionally substituted by one or more substituent(s) selected from the group consisting of halo, C$_{1-7}$-alkyl, 017 alkoxy, hydroxy, phenyl and di(C$_{1-7}$)alkylamino; and
R$^3$ is H, C$_{1-7}$-alkyl, or C$_{3-6}$-cycloalkyl;
or an optical isomer or pharmaceutically acceptable salt thereof.

2. The compound of claim 1, wherein:
R$^1$ is phenyl optionally substituted by one or more substituents selected from the group consisting of Cl, F and C$_{1-7}$-haloalkyl,
or is morpholine or piperidine each of which is optionally substituted by OH;
R$^2$ is Br, I, C$_{1-7}$-haloalkoxy, C$_{3-6}$-cycloalkyl optionally substituted by phenyl, morpholine or piperidine; and
R$^3$ is C$_{1-7}$-alkyl;
or an optical isomer or pharmaceutically acceptable salt thereof.

3. The compound of claim 2, wherein the compound is selected from the group consisting of:
3-Methanesulfonyl-2-methyl-4-phenyl-6-trifluoromethoxy-quinoline;
6-Bromo-3-methanesulfonyl-2-methyl-4-phenyl-quinoline;
3-Methanesulfonyl-2-methyl-4-phenyl-6-piperidin-1-yl-quinoline;
3-Methanesulfonyl-2-methyl-6-morpholin-4-yl-4-phenyl-quinoline;
6-Bromo-4-(4-fluoro-phenyl)-3-methanesulfonyl-2-methyl-quinoline;
4-(4-Fluoro-phenyl)-3-methanesulfonyl-2-methyl-6-morpholin-4-yl-quinoline;
6-Bromo-4-(4-chloro-phenyl)-3-methanesulfonyl-2-methyl-quinoline;
4-(4-Chloro-phenyl)-3-methanesulfonyl-2-methyl-6-morpholin-4-yl-quinoline;
3-Methanesulfonyl-2-methyl-6-morpholin-4-yl-4-(4-trifluoromethyl-phenyl)-quinoline;
3-Methanesulfonyl-2-methyl-6-morpholin-4-yl-4-(2,4,5-trifluoro-phenyl)-quinoline;
6-Bromo-3-methanesulfonyl-2-methyl-4-(4-trifluoromethyl-phenyl)-quinoline; and
6-Bromo-3-methanesulfonyl-2-methyl-4-(2,4,5-trifluoro-phenyl)-quinoline.

4. The compound of claim 1, wherein R$^1$ is phenyl optionally substituted by one or more substituents selected from the group consisting of halogen and C$_{1-7}$-haloalkyl.

5. The compound of claim 1, wherein R$^1$ is a 5 or 6 membered heterocycloalkyl optionally substituted by OH.

6. The compound of claim 5, wherein R$^1$ is morpholine.

7. The compound of claim 6, wherein the compound is selected from the group consisting of:
6-Iodo-3-methanesulfonyl-2-methyl-4-morpholin-4-yl-quinoline;
6-Bromo-3-methanesulfonyl-2-methyl-4-morpholin-4-yl-quinoline;
3-Methanesulfonyl-2-methyl-4-morpholin-4-yl-6-((1R,2R)-2-phenyl-cyclopropyl)-quinoline;
3-Methanesulfonyl-2-methyl-4-morpholin-4-yl-6-piperidin-1-yl-quinoline; and
6-Cyclopropyl-3-methanesulfonyl-2-methyl-4-morpholin-4-yl-quinoline.

8. The compound of claim 5, wherein R$^1$ is piperidine optionally substituted by OH.

9. The compound of claim 8, wherein the compound is selected from the group consisting of:
6-Iodo-3-methanesulfonyl-2-methyl-4-piperidin-1-yl-quinoline;
1-(6-Iodo-3-methanesulfonyl-2-methyl-quinolin-4-yl)-piperidin-4-ol;
(R)-1-(6-Iodo-3-methanesulfonyl-2-methyl-quinolin-4-yl)-piperidin-3-ol; and
(S)-1-(6-Iodo-3-methanesulfonyl-2-methyl-quinolin-4-yl)-piperidin-3-ol.

10. The compound of claim 1, wherein R2 is Br, I, C1-7-alkyl, C1-7-alkoxy, C 1-7-haloalkyl, C1-7-haloalkoxy.

11. The compound of claim 10, wherein R2 is Br or I.

12. The compound of claim 10, wherein R2 is C1-7-alkoxy.

13. A compound of claim 1, wherein R2 is aryloxy or arylsulfonyl.

14. A compound of claim 1, wherein R2 is cycloalkyl optionally substituted by phenyl.

15. The compound of claim 1, wherein R2 is —NRaRb.

16. The compound of claim 15, wherein Ra and Rb are each independently C1-7-alkyl.

17. The compound of claim 15, wherein Ra and Rb, together with the nitrogen atom to which they are attached, form a 4 to 8 membered heterocycloalkyl group which is optionally substituted by one or more substituent selected from the group consisting of halo, C1-7-alkyl, C1-7-alkoxy, hydroxy, phenyl and di(C1-7-alkyl)amino.

18. A compound of claim 17, wherein —NRaRb is piperidine.

19. A compound of claim 17, wherein —NRaRb is morpholine.

20. The compound of claim 1 having formula I-a:

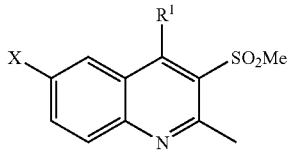

I-a wherein
R$^1$ is a 5 or 6 membered heterocycloalkyl ring optionally substituted by OH, and
X is Br or I.

21. The compound of claim 1 having formula I-b:

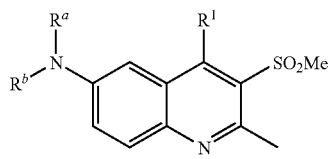

I-b wherein
R$^1$ is a 5 or 6 membered heterocycloalkyl ring optionally substituted by OH.

22. The compound of claim 1 having formula I-c:

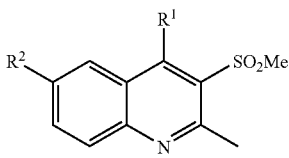

I-c wherein
R$^1$ is a 5 or 6 membered heterocycloalkyl ring optionally substituted by OH.

23. A compound selected from the group consisting of:
(2-Amino-5-bromo-phenyl)-(4-trifluoromethyl-phenyl)-methanone;
(2-Amino-5-bromo-phenyl)-(2,4,5-trifluoro-phenyl)-methanone;
6-Bromo-2-methyl-4H-3,1-benzoxazin-4-one;
6-Iodo-2-methyl-4H-3,1-benzoxazin-4-one;
6-Bromo-3-methanesulfonyl-2-methyl-quinolin-4-ol;
6-Iodo-3-methanesulfonyl-2-methyl-quinolin-4-ol;
6-Bromo-4-chloro-3-methanesulfonyl-2-methyl-quinoline; and
4-Chloro-6-iodo-3-methanesulfonyl-2-methyl-quinoline.

24. A composition comprising a therapeutically effective amount of a compound of formula I:

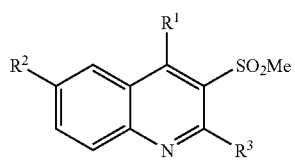

(I)

wherein
R$^1$ is phenyl optionally substituted by one or more substituents selected from the group consisting of Cl, F, C$_{1-7}$-haloalkyl, hydroxy, C$_{1-7}$-alkoxy, C$_{1-7}$-haloalkoxy, di(C$_{1-7}$)alkylamino and C$_{1-7}$-alkylsulfonyl,
or is 5 or 6 membered heterocycloalkyl optionally substituted by OH;
R$^2$ is Br, I, C$_{1-7}$-alkyl, C$_{1-7}$ alkoxy, C$_{1-7}$-haloalkyl, C$_{1-7}$-haloalkoxy, aryloxy, arylsulfonyl, C$_{3-6}$-cycloalkyl optionally substituted by phenyl, or —NR$^a$R$^b$ wherein R$^a$ and R$^b$ are each independently C$_{1-7}$-alkyl, or R$^a$ and R$^b$, together with the nitrogen atom to which they are attached, form a 4 to 8 membered heterocycloalkyl group which is optionally substituted by one or more substituent(s) selected from the group consisting of halo, C$_{1-7}$-alkyl, C$_{1-7}$ alkoxy, hydroxy, phenyl and di(C$_{1-7}$)alkylamino; and
R$^3$ is H, C$_{1-7}$-alkyl, or C$_{3-6}$-cycloalkyl; or a pharmaceutically acceptable salt thereof and a pharmaceutically acceptable carrier.

\* \* \* \* \*

UNITED STATES PATENT AND TRADEMARK OFFICE
CERTIFICATE OF CORRECTION

PATENT NO.       : 7,728,142 B2                                    Page 1 of 1
APPLICATION NO.  : 11/444770
DATED            : June 1, 2010
INVENTOR(S)      : Malherbe et al.

It is certified that error appears in the above-identified patent and that said Letters Patent is hereby corrected as shown below:

Claim 1, Column 23, line 47: "halo, $C_{1-7}$-alkyl, 017 alkoxy," should read
-- halo, $C_{1-7}$-alkyl, $C_{1-7}$-alkoxy, --.

Signed and Sealed this

Thirteenth Day of July, 2010

David J. Kappos
*Director of the United States Patent and Trademark Office*